United States Patent [19]
Rowe

[11] Patent Number: 5,206,672
[45] Date of Patent: Apr. 27, 1993

[54] SURGICAL OPTOMETER

[75] Inventor: Temple S. Rowe, Mission Viejo, Calif.

[73] Assignee: Nestle S.A., Switzerland

[21] Appl. No.: 577,514

[22] Filed: Sep. 5, 1990

[51] Int. Cl.$^5$ .............................................. A61B 3/10
[52] U.S. Cl. ................................... 351/212; 351/211; 351/205; 351/221
[58] Field of Search ............... 351/205, 211, 212, 221; 356/135

[56] References Cited

U.S. PATENT DOCUMENTS

| | | |
|---|---|---|
| 3,036,568 | 5/1962 | Stark . |
| 3,536,383 | 10/1970 | Cornsweet et al. . |
| 3,572,909 | 3/1971 | VanPatten et al. . |
| 3,762,821 | 10/1973 | Bruning et al. . |
| 3,930,732 | 1/1976 | Holly . |
| 4,021,102 | 5/1977 | Iizuka . |
| 4,353,625 | 10/1982 | Nohda et al. . |
| 4,367,019 | 1/1983 | Kitao et al. . |
| 4,372,655 | 2/1983 | Matsumura et al. . |
| 4,390,255 | 6/1983 | Nohda et al. . |
| 4,421,391 | 12/1983 | Matsumura et al. . |
| 4,591,247 | 5/1986 | Kamiya et al. . |
| 4,620,318 | 10/1986 | Hill . |
| 4,637,700 | 1/1987 | Krueger . |
| 4,678,297 | 7/1987 | Ishikawa et al. . |
| 4,744,648 | 5/1988 | Kato et al. . |
| 4,755,041 | 7/1988 | Ishikawa et al. . |
| 4,761,070 | 8/1988 | Fukuma . |
| 4,834,528 | 5/1989 | Howland et al. . |

*Primary Examiner*—Bruce Y. Arnold
*Assistant Examiner*—Hung Xuan Dang
*Attorney, Agent, or Firm*—James Arno; Jeffrey S. Schira; Christopher Brody

[57] ABSTRACT

There are disclosed an improved method and apparatus which derive the optical characteristics of a lens system from a plurality of measurement beams and can display the same. Included is an imaging channel which cooperates with a microprocessor for detecting the measurement beams and processing the detected beam information to derive the optical characteristics of the lens system.

12 Claims, 2 Drawing Sheets

SURGICAL OPTOMETER

BACKGROUND OF THE INVENTION

The present invention relates generally to a method of and apparatus for testing an optical system and, more particularly, to an improved method of and apparatus for measuring the optical properties of a cornea/intra-ocular lens system.

In the ophthalmological field, it is highly desirable to have a device which measures accurately the optical properties of a cornea and/or human eye optical lens system independent of input of the person whose eyes are being examined. This would be especially useful for pediatric and geriatric patients.

There are a number of instruments which have been proposed for testing the optical properties of patients' eyes and exemplary ones are described in U.S. Pat. Nos.: 3,536,383; 4,353,652; 4,390,255; 4,367,019; 4,367,700; 4,372,655; 4,421,391; and 4,591,247. For example, U.S. Pat. No. 3,930,732 describes an apparatus for testing the optical transfer function of a lens system which employs a laterally moving fringe pattern produced by convergence of two monochromatic coherent-radiation beams. Several components are required to be rotated or otherwise moved. For instance, U.S. Pat. No. 4,367,019 relates to an eye refractometer which includes a system for projecting a target onto the fundus of the eye. The target is rotated to determine one astigmatic axis. This allows for determination of the eye's refractive power along one axis. The target is rotated for 90° to measure the refractive power along the other astigmatic axis. The foregoing group of devices, however, rely on moving components for purposes of effecting cornea and intra-ocular optical measuring functions.

It is clear that there are disadvantages associated with having high precision instruments requiring moving components. In this regard, there are significant cost and construction factors to take into account not to mention demanding calibration considerations, which must be obtained and maintained during use of such an instrument. These latter considerations are especially important given the degree of accuracy necessary for measuring the optical properties of the human eye. Beyond these considerations, however, there is also a desire to provide a measuring instrument which also reduces greatly the work and time involved in evaluating the information received, while minimizing subjective judgments of the person evaluating the information.

SUMMARY OF THE INVENTION

According to the present invention there are provided an improved method of and apparatus for testing the optical properties of an optical system.

Included in the method of testing optical properties of an optical system are: a step of providing a plurality of stationary measurement beams of collimated radiant energy; a step of dividing the collimated beams into measurement and reflected fixed paths, and directing the measurement beams along the measuring path toward the optical system; a step of detecting by stationary detecting areas each of the plurality of reflected measurement beams travelling along the reflected path from the optical system and providing a signal of each reflected beam; and, a step of processing each of the signals of the reflected beams and generating at least a signal representative of an optical property of the optical system based on the signals of the reflected measurement beams.

In an illustrated embodiment, the method further comprises the step of displaying a value of the optical property of the optical system represented by the generated signal.

In another illustrated embodiment, the method step of dividing the collimated measurement beams includes the step of providing a third path, and further comprises the step of detecting the power of the measurement beams along the third path for facilitating calibration of each of the beams to ensure that each beam is of substantially equal power.

In another illustrated embodiment, the processing step processes the signals of the reflected measurement beams so as to derive different optical characteristics of the optical system, wherein one characteristic is the refractive power of the cornea/intra-ocular lens system.

Also in accordance with the present invention provision is made for an apparatus for testing optical properties of an optical system. Included are means for providing a plurality of stationary measurement beams of collimated radiant energy; means for dividing the collimated measurement beams into fixed measurement and reflected paths, and directing the measurement beams along a measurement path toward the optical system; means for detecting by stationary detecting areas each of the plurality of reflected measurement beams travelling along the reflected path from the optical system and providing a signal of each reflected beam; and, means for processing each of the signals of the reflected beams and generating at least a signal representative of an optical property of the optical system based on the signals of the reflected measurement beams.

Among the other objects and features of the present invention are the provisions of an improved method of and apparatus for testing optical properties of a lens system; the provisions of an improved method of and apparatus for measuring the optical properties of a lens system without the apparatus having moving components for effecting the measuring functions; the provisions of an improved method of and apparatus of the last noted types for measuring the optical properties of a cornea/intra-ocular lens system; the provisions of an improved method of and apparatus of the last noted types for measuring the optical properties of a cornea/intra-ocular lens system without the input of the person being examined; the provisions of an improved method of and apparatus for measuring the optical properties of a cornea/intra-ocular lens system in a manner which minimizes subjective interpretation of information; the provisions of an improved method of and apparatus for achieving the foregoing while reducing greatly the work and time involved in evaluating information; the provisions of an improved method of and apparatus for use as a surgical optometer and autorefractometer; the provisions of an improved method of and apparatus for use as an autocollimator; and, the provisions of an improved method and apparatus of the above noted kinds which achieve the foregoing noted advantages in a relatively simple and inexpensive manner.

Still other objects and further scope of applicability of the present invention will become apparent from the detailed description to follow when taken in conjunction with the accompanying drawings in which like parts are designated by like reference numerals throughout the several views.

DETAILED DESCRIPTION

Figure 1:
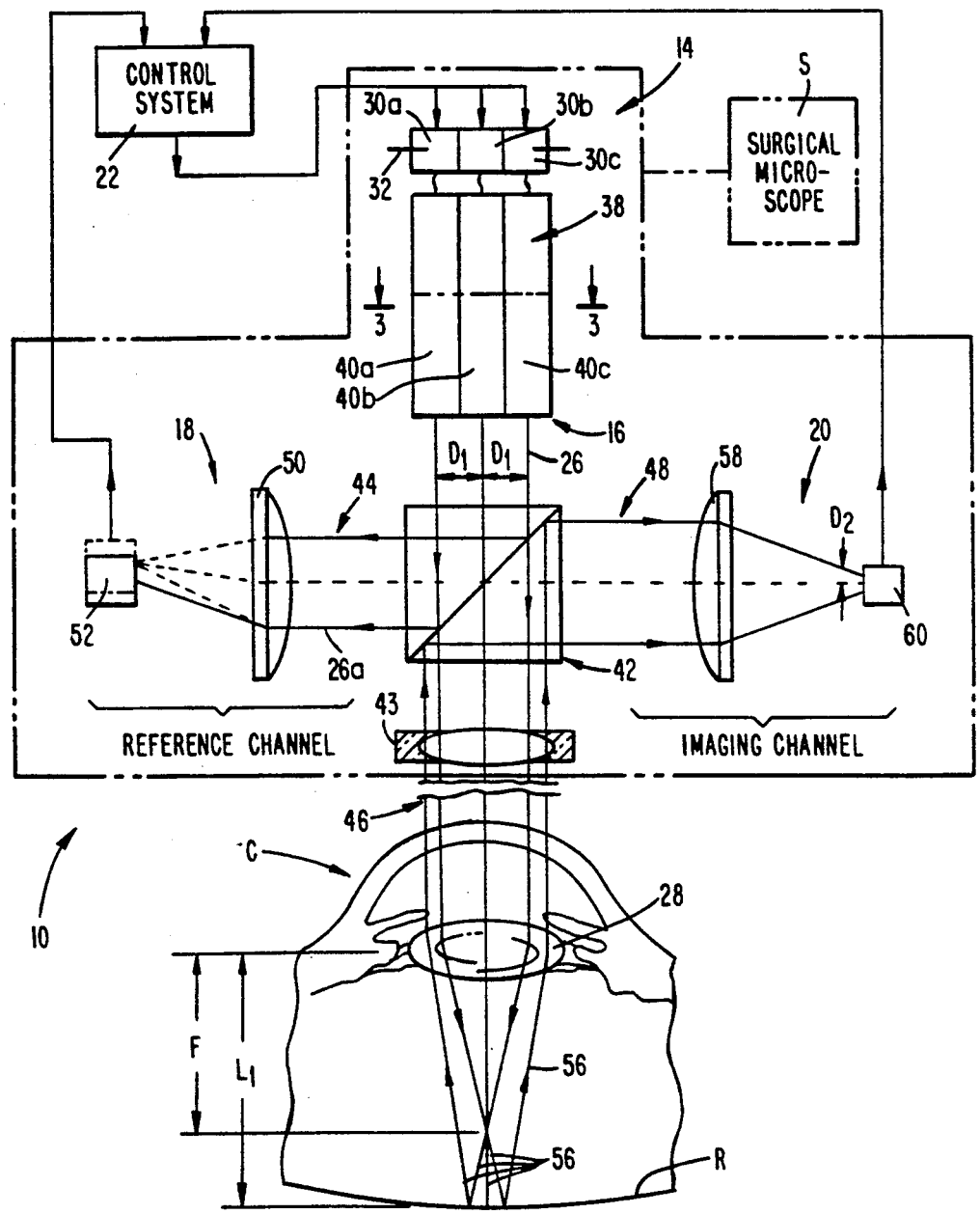
FIG. 1 is a diagrammatic view of an improved apparatus for measuring the optical properties of an ocular lens system.
Figure 2:
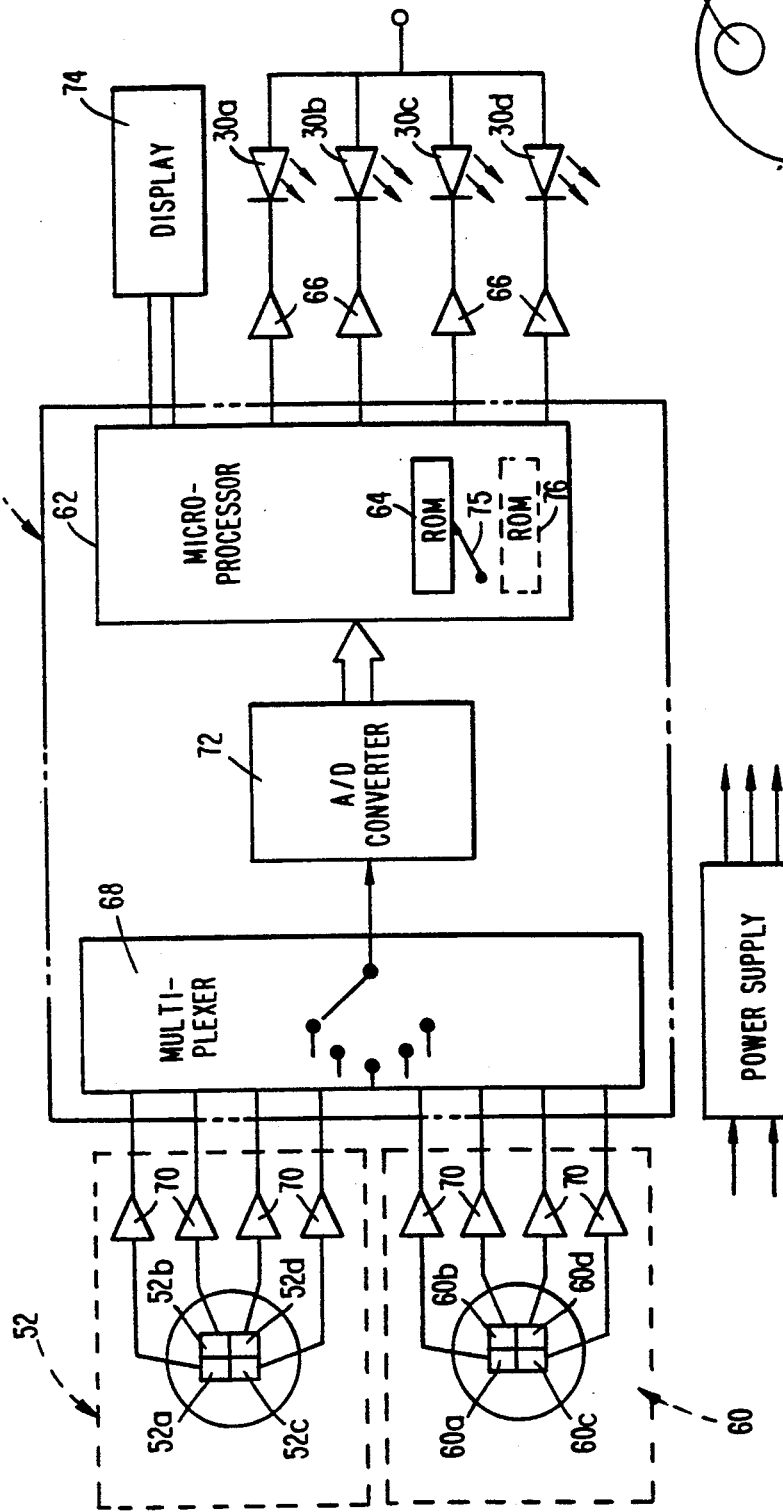
FIG. 2 is a block diagram of the electrical components forming the apparatus of the present invention.
Figure 3:
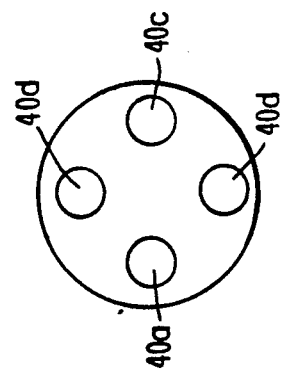
FIG. 3 is a cross-sectional view along section line 3—3 of FIG. 1 disclosing an arrangement of light-emitting diodes for use in the present invention.

Reference is made to FIGS. 1-3 for showing, in diagrammatic form, one preferred form of an apparatus made according to this invention. In this embodiment, the apparatus is a surgical optometer 10 which includes a housing assembly designated generally by reference numeral 12. Included in the housing assembly 12 are: a reference or test beam generating assembly 14; a light beam collimating and directing assembly 16; a reference channel assembly 18; an imaging channel assembly 20; and, a control system 22 having connected thereto a display assembly 24. Although this embodiment is disclosed for use as an optometer, it can be used as an autorefractometer as well.

The optometer housing assembly 12 can be attached to a known type of surgical microscope, designated generally by reference letter S, which allows a user to manipulate the optometer 10 relative to a patient's cornea/intra-ocular lens system of the human eye C for performing the measuring functions to be described. The surgical microscope S can be of the type which is commercially available from Möller-Wedel or any surgical microscope manufacturer. There is little difficulty in effecting the connection between the optometer 10 and microscope S, since the former operates independently of the latter. Other devices can be used for mounting and moving the optometer 10 at the surgical site, such as any floorstand or ceiling mount. Details of such attachment have not been provided since they do not form an aspect of the present invention.

Reference is now made to the measurement beam generating assembly 14 which is selectively operable by the control system 22 to generate a plurality of measurement beams 26 which are used for testing the optical properties of an intra-ocular lens 28. The measurement beams 26 are generated by a plurality of infrared light-emitting diodes 30 $a$–$d$. The light-emitting diodes 30 $a$–$d$ provide for constant and generally coequal intensity outputs. A non-visible frequency is used and is about 780 nm in the near infrared range. Other visible and invisible frequency radiation sources can be used (e.g., ultraviolet). The light-emitting diodes 30 $a$–$d$ are mounted on a stationary support structure 32 and are spaced apart generally circumferentially from each other by about 90°. For purposes of illustration and not limitation, each of the diodes 30 $a$–$d$ has a light emitting surface area in a range of about 1 to 10 microns and in this embodiment is 10 microns. Larger emitting areas can also be used. While four light-emitting diodes 30 $a$–$d$ have been disclosed other numbers of light-emitting diodes and photodetectors areas can be utilized. The number of light-emitting diodes and the number of photo-detector elements do not have to correspond. As will be explained in detail below, the infrared light-emitting diodes 30 $a$–$d$ are sequentially driven. For each measuring cycle, the light-emitting diodes 30 $a$–$d$ are energized for about 5 msec and at 50 msec intervals. These values are for illustration purposes and not limitation. Ideally, the intensities of the light-emitting diodes 30 $a$–$d$ are constant so that the detected information can be electronically processed without additional memory. It is, however, within the scope of the invention to have each light-emitting diode provide different intensity outputs, so long as the control system 22 compensates for known variations in the intensities of the emitted reference beams 26.

Reference is now made to the light beam collimating and directing assembly 16 which transfers the reference beams 26 toward the cornea/intra-ocular lens of the human eye C. Included in the assembly 16 is a fiber optic bundle 38, collimating gradient index lenses 40 $a$–$d$ and a beamsplitter 42. The fiber optic bundle 38 is comprised of a plurality of fiber optic pigtails which are positioned in front of the light-emitting diodes 30 $a$–$d$. It will be appreciated that this invention envisions other sources of radiation for the measurement beams 26, such as laser diodes. Adjacent the fiber optic bundle 38 is a plurality of correspondingly spaced collimating gradient index (GRIN) lenses 40 $a$–$d$ (FIG. 3). Each of the lenses 40 $a$–$d$ is optically aligned to corresponding ones of the light-emitting diodes 30 $a$–$d$. The lenses 40 $a$–$d$ and a delivery optical system indicated generally by reference numeral 43 are appropriately selected so as to focus the collimated measurement beams 26 onto the retina R which is a diffuse reflector.

The beamsplitter 42 is positioned suitably in the optical path of the collimated measurement beams 26 for dividing the latter into a plurality of different optical paths 44, 46 and 48 (FIG. 1). The beamsplitter 42 is a cube optic having an internal hypotenuse coated to reflect 50% and to transmit 50% of the incident infrared light. The outer surfaces of the cubes have an antireflection coating. The path 44 defines a reference channel path which extends from the beamsplitter 42 through the reference channel assembly 18. That portion of the measurement beams 26 travelling to the photodetector 52 are considered reference beams 26$a$. The path 46 extends along an optical axis through the beamsplitter 42, through the delivery optical system 43, to the cornea/intra-ocular lens of the human eye C and is considered the measurement path. The path 48 is considered the reflected path and is coincidental to a portion of the measurement path, from the retina to the beamsplitter, and a portion which extends perpendicular to the path 46 and along which travels the reflected measurement beams through the imaging channel assembly 20.

Included in the reference channel assembly 18 is a reference lens 50 which is focused on the quadrant photodetector 52 that is located at the focal plane of the reference lens. Essentially, the quadrant cell detector 52 has four photocells 52 $a$–$d$, each of which is arranged to detect a portion of the power of each reference beam for generating a signal representative of spatial information for transmission to the control system 22.

Once the measurement beams 26 strike the retina R, they will be reflected back along the path 46 toward the beamsplitter 42. The reflected measurement beams 56 are then transmitted along the imaging channel path 48 toward an imaging lens 58 which directs the reflected measurement beams 56 onto the quadrant cell detector 60 which has four photocells 60 $a$–$d$. The quadrant cell detector photocells 60 $a$–$d$ also serve to detect a portion of the power of each of the reflected measurement beams 56 incident thereon for subsequent transmission to the control system 22.

Reference is now made to the block circuit diagram of FIG. 2 for describing the operation of the surgical optometer 10.

In one mode of operation of the present invention the apparatus is used as an optometer for intra-operatively testing the cornea/intra-ocular refractive power and astigmatism, as well as to intra-operatively test the cornea/IOL refractive and astigmatic power combination. In another mode, the invention could be used to test any lens/mirror combination, such as an autocollimator would. The mode to be described presently will focus on use of the invention as an optometer.

The optometer 10 must be initially centered on the pupil of each eye to be examined. In this connection there is provided an initial centering operation, wherein use is made of a known type of calibration shield (not shown). The shield is typically placed over the patient's eye to check the return energy for each reflected measurement beam 56 on the imaging quadrant cell detector 60. If the sum of signals of each of the cells 60 a-d in this measuring cycle are equal for each beam, the shield is removed and the surgical microscope is aligned to the dilated (3.5 mm) pupil. Equal sums of the signals for each respective measurement beam 56 is indicative of the fact that the optometer is centered on the patient's pupil, i.e., equal vignetting of each of the measurement beams passing through the pupil.

For commencing the initial measuring or centering cycle of an overall operating cycle, a switch (not shown) is actuated which energizes the control system 22, wherein a microprocessor 62 is operable to effectuate such a cycle. In this regard, the microprocessor 62 includes a read-only memory (ROM) 64 which contains a program or set of instructions for the optometer 10 to follow. During such a cycle, each of the light-emitting diodes 30 a-d is sequentially energized by known current regulated drive electronics circuitry including analog amplifiers 66. In this embodiment it is desired to have the intensity of the emitted measurement beams 26 equal. In this manner each of the cells 52 a-d of the quadrant cell detector 52 can measure a portion of the power of each reference beam 26a travelling along the reference path 44. The signals outputted from each quadrant cell 52 a-d are transmitted to an analog-multiplexer 68 through an analog/amplifier 70. The multiplexer output signals are processed by the analog/digital converter 72 and transmitted to the microprocessor 62. The microprocessor 62 evaluates each input relative to a predetermined value. Should variations exist, the microprocessor 62 through the amplifiers 66 appropriately effects raising or lowering of the current supplied to respective ones of the light-emitting diodes 30 a-d. Accordingly, uniformity of their outputs is insured. This type of feedback compensates for age as well as thermal and transmission differences of each of the light-emitting diodes 30 a-d. Uniformity of output is advantageous since it simplifies the data processing involved.

As noted, once the signals from the beams 56 are equal the shield is removed. In this condition, the microprocessor 62 is operable to energize a display apparatus 74 to energize a light (not shown) indicating to an operator that centering has been achieved. This display may also be integrated into the surgical microscope and viewed through the microscope oculars (e.g., "Heads-Up Display"). Once the initial centering operation is complete the optometer is ready to commence the testing of corneal lens optical properties. Although a visual display apparatus is preferred it is within the spirit of this invention that the microprocessor 62 could operate an associated printer for printing the information as well as for displaying the same.

In this testing portion of an overall operating cycle, the measurement beams 56 are transmitted through the beamsplitter 42 and impinge upon the retina R, such that the incident radiation is reflected back as reflected beams 56 toward the imaging channel assembly 20. The measurement lens 58 is effective to focus the reflected beams 56 onto of the cells 60 a-d. The corresponding signals generated by each cell is forwarded through the amplifiers 70 to the multiplexer 68. From the multiplexer 68 the signals are then transmitted to the microprocessor 62 through the analog/digital convertor 72. In the microprocessor 62 the ROM 64 is operable for evaluating the information of the reflected measurement beams 56 relative to the information of the reference beams gathered by the reference channel assembly 18 to determine the optical characteristics of the corneal optical system.

It will be understood that when the optometer 10 is aligned an optically correct corneal/IOL optical system will refract the collimated measurement beams to a single point (not shown) on the retina. Accordingly, the reflected measurement beams 56 will retrace their original ray path back to the beamsplitter 42 and then along the path 48 to the measurement lens 58. The measurement lens 58 refracts the rays of the respective reflected measurement beams 56 onto the quadrant cell detector 60. Perfect refraction is indicated when the signals of each of the cells 60 a-d are equal for each measurement beam. The signals will be equal because all the reference beams will be centered on the quadrant photodetector 60. Of course, the signals of each of the cells 60 a-d are outputted through the multiplexer 68 to the microprocessor 62. The ROM 64 of the microprocessor 62 has instructions to compare the signals and will produce a net zero signal vector indicating perfect refraction conditions. Moreover, the existence of such condition leads to the microprocessor energizing the alphanumeric displays (not shown) to read, for example, 0.00D spherical, 0.00D cylinder, 0.0 degree rotation.

On the other hand, for imperfect refraction of the cornea/intra-ocular lens of the human eye system C the measurement beams 26 do not coincide on the retina R. As a consequence, the chief ray of the reflected measurement beams 56 travel to the imaging channel assembly 18 where they will be imaged onto the cells 60 a-d at a slight angle with respect to the optical centerline for perfect refraction. Such displacement or refractive error can be determined by the following formula:

Refractive error = D2 = D1 (L/f − 1)

wherein D1 = the distance (in a common horizontal plane) between the chief ray of each of the GRIN lenses and the centroid of the GRIN lens cluster;
 f = the focal distance of the optical system
 L = the distance of the retina from the lens Displacement of each reflected beam 56 creates signals which will be unequal to the signals from the other cells. Each signal of respective ones of the cells 60 a-d which correspond to one of the measurement beams is stored in a memory (not shown) of the microprocessor 62 for subsequent manipulation as will be described.

The ROM 64 is then effective to perform a vector manipulation to derive a net sum vector by vector addition. The sum vector is equivalent to the magnitude and direction (angle) of the cylindrical refractive error. The spherical refractive error is simply the average of the absolute values of the vectors aligned to the minor axis of the cylinder. Astigmatism is simply the additional refractive power measured along the major axis of the cylinder. The angle of rotation (with the rule) of the astigmatic axis is simply the angle component (0°–180°) of the net sum vector. The vector manipulation can be performed digitally by analog-to-digital converters (not shown) and arithmetic processors (not shown) in known ways. Moreover, the microprocessor 62 is effective to operate alphanumeric displays on the display 74 for visually indicating the values noted above. The display can be operable to provide other information.

In this manner, the refractive power of the patient's eye can be determined without input from the patient. The microprocessor 62 can also have other read-only memories which can perform other manipulations with the vector information, such as determining astigmatism. The computation would be based on the vector information input of each reflected reference beam 56. The present invention can also be used as an autocollimator for testing the lenses and mirrors of an optical system. This would be done by placing any optical system consisting of a lens or mirror and a diffuse reflector into the path of the measurement beams.

Selection of the different modes of operation can be accomplished by means of a mode selection switch 75, FIG. 2, with different modes established by the ROM's. The switch 75 effectively cooperates the system with respective ones of the ROMs. Specifically, the ROM 64 establishes use of the apparatus as a surgical optometer, while ROM 76 establishes use of the apparatus as an autocollimator for testing lens/mirror combinations.

Since certain changes may be made in the above-described methods and apparatus without departing from the scope of the invention herein involved, it is intended that all matter contained in the description or shown in the accompanying drawings shall be interpreted as illustrative and not in a limiting sense.

What is claimed is:

1. A method of testing optical properties of an optical system comprising the steps of:
   providing a plurality of stationary measurement beams of collimated radiant energy as collimated measurement beams;
   dividing the collimated measurement beams into at least a measurement fixed path and a reference channel path, and directing the beams traveling along the measurement fixed path toward the optical system;
   stationarily detecting each of a plurality of reflected measurement beams reflected from the optical system and traveling along a reflected fixed path from the optical system and providing a signal of each reflected measurement beam; and,
   processing each of the signals of the reflected measurement beams and generating at least a signal representative of an optical property of the optical system based on the signals of the reflected beams;
   detecting the intensity of measurement beams travelling along the reference channel path for facilitating calibration of each of the beams to ensure that the beams are of substantially equal intensity.

2. The method of claim 1 wherein said processing step processes the signals of the reflected measurement beams so as to derive different optical characteristics of the optical system.

3. A method of testing optical properties of a corneal lens system comprising the steps of:
   providing a plurality of stationary beams of collimated radiant energy a collimated beams;
   dividing the collimated beams into at least a measurement fixed path, and a reference channel path and directing the beams traveling along the measurement fixed path toward the cornea lens system;
   stationarily detecting each of a plurality of reflected measurement beams reflected from said corneal lens system and traveling along a reflected path from the corneal lens system and providing a signal of each reflected measurement beam;
   processing each of the signals of the reflected beams and generating at least a signal representative of an optical property of the lens system based on the signals generated by the reflected measurement beams;
   detecting the intensity of measurement beams traveling along the reference channel path for facilitating calibration of each of the measurement beams to ensure that the measurement beams are of substantially equal intensity and are spatially invariant.

4. The method of claim 3 wherein said processing step processes the signals of the reflected measurement beams so as to derive different optical characteristics of the lens system.

5. The method of claim 4 wherein:
   said step of providing a plurality of measurement beams utilizes non-visible frequencies for the beams.

6. The method of claim 5 wherein:
   said processing step processes information from the reflected beams and determines the refractive power of the lens system.

7. The method of claim 6 wherein:
   said processing step processes information from the reflected beams which determines astigmatism characteristics of the lens system.

8. An apparatus for testing optical properties of an optical system comprising:
   means for providing a plurality of stationary beams of collimated radiant energy as collimated measurement beams;
   means for dividing the collimated measurement beams into at least reflected and measurement fixed paths, and a reference channel path and for directing the collimated beams travelling along the measurement fixed path toward the optical system;
   means for stationarily detecting each of a plurality of reflected beams reflected from the optical system and travelling along the reflected path from the optical system and providing a signal of each reflected beam;
   means for processing each of the signals of the reflected beams and generating at least a signal representative of an optical property of the optical system based on the signals generated by the reflected beams;
   means for detecting the intensity of measurement beams travelling along the reference channel path for facilitating calibration of each of the beams to ensure that the beams are of substantially equal intensity and are spatially invariant.

9. The apparatus of claim 8 wherein said processing means processes the signals of the reflected measurement beams so as to derive different optical characteristics of the optical system.

10. The apparatus of claim 9 wherein:
said means for providing a plurality of measurement beams utilizes non-visible frequencies for the beams.

11. The apparatus of claim 9 wherein:
said processing means is operable for processing information from the reflected beams which determines the refractive power of optical system.

12. Apparatus for testing optical properties of a corneal lens system comprising:
means for providing a plurality of stationary beams of collimated radiant energy as collimated beams;
means for dividing the collimated beams into at least reflected and measurement fixed paths, and a reference channel path and for directing the collimated beams travelling along the measurement path toward the cornea lens system;
means for stationarily detecting each of a plurality of reflected measurement beams reflected from said lens system and travelling along the reflected fixed path from the corneal lens system and providing a signal of each reflected beam;
means for processing each of the signals of the reflected measurement beams and generating at least a signal representative of an optical property of the lens system based on the signals generated by the reflected measurement beams;
means for detecting intensity of the collimated beams travelling along the reference channel path for facilitating calibration of each of the collimated beams to ensure that the collimated measurement beams are of substantially equal intensity and are spatially invariant.

* * * * *

UNITED STATES PATENT AND TRADEMARK OFFICE
CERTIFICATE OF CORRECTION

PATENT NO. : 5,206,672
DATED : April 27, 1993
INVENTOR(S) : T. Scott ROWE et al

It is certified that error appears in the above-indentified patent and that said Letters Patent is hereby corrected as shown below:

<u>Title page</u>, item [75], Inventor, please insert as a second inventor --David Dewey, Sunnyvale, Calif.-- after "Temple S. Rowe, Mission Viejo, Calif".

Signed and Sealed this

Twenty-ninth Day of November, 1994

Attest:

BRUCE LEHMAN

Attesting Officer

Commissioner of Patents and Trademarks